(12) United States Patent
Langford

(10) Patent No.: US 9,089,880 B2
(45) Date of Patent: *Jul. 28, 2015

(54) APPARATUS AND METHOD FOR REPROCESSING LUMENED INSTRUMENTS

(71) Applicant: Langford IC Systems, Inc., Tucson, AZ (US)

(72) Inventor: Terrence R. Langford, Tucson, AZ (US)

(73) Assignee: Langford IC Systems, Inc., Tuscon, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,023

(22) Filed: Jun. 16, 2014

(65) Prior Publication Data

US 2014/0290700 A1 Oct. 2, 2014

Related U.S. Application Data

(63) Continuation-in-part of application No. 14/152,789, filed on Jan. 10, 2014, which is a continuation of application No. 12/247,830, filed on Oct. 8, 2008, now Pat. No. 8,658,090, which is a continuation-in-part of application No. 11/367,787, filed on Mar. 3, 2006, now abandoned.

(51) Int. Cl.

| | |
|---|---|
| *B08B 9/032* | (2006.01) |
| *A61B 1/12* | (2006.01) |
| *A61B 19/00* | (2006.01) |
| *A61L 2/14* | (2006.01) |
| *A61L 2/16* | (2006.01) |
| *A61L 2/18* | (2006.01) |
| *A61L 2/24* | (2006.01) |
| *A61L 2/07* | (2006.01) |
| *A61L 2/20* | (2006.01) |

(52) U.S. Cl.
CPC .............. *B08B 9/0321* (2013.01); *A61B 1/123* (2013.01); *A61B 19/34* (2013.01); *A61L 2/14* (2013.01); *A61L 2/16* (2013.01); *A61L 2/18* (2013.01); *A61L 2/24* (2013.01); *A61B 2019/343* (2013.01); *A61L 2/07* (2013.01); *A61L 2/206* (2013.01); *A61L 2202/122* (2013.01); *A61L 2202/24* (2013.01); *B08B 2209/022* (2013.01)

(58) Field of Classification Search
CPC ........ B08B 9/0321; A61B 1/123; A61L 2/14; A61L 2/16; A61L 2/18; A61L 2/24
See application file for complete search history.

(56) References Cited

U.S. PATENT DOCUMENTS

| | | |
|---|---|---|
| 2,965,936 A | 12/1960 | Kaye |
| 3,383,163 A | 5/1968 | Menashi |

(Continued)

FOREIGN PATENT DOCUMENTS

| | | |
|---|---|---|
| EP | 09819648.8 | 3/2012 |
| WO | WO 02/43780 | 6/2002 |

*Primary Examiner* — Regina M Yoo
(74) *Attorney, Agent, or Firm* — Quarles & Brady LLP; Gavin J. Milczarek-Desai

(57) ABSTRACT

Apparatus and methods for processing an item, such as a lumened instrument, secured in a connectorless fashion in a push/pull reprocessor. The push/pull reprocessor includes a container having a first chamber and a second chamber and a pressure sensor in each chamber such that the method includes the step of generating a flow of a liquid, such as ozonated water, back-and-forth upon the item or additionally through a lumen in the case of a lumened instrument.

20 Claims, 5 Drawing Sheets

(56) References Cited

U.S. PATENT DOCUMENTS

| | | |
|---|---|---|
| 3,851,436 A | 12/1974 | Fraser et al. |
| 3,948,601 A | 4/1976 | Fraser et al. |
| 4,197,917 A | 4/1980 | Langford et al. |
| 5,184,633 A | 2/1993 | Langford |
| 5,207,237 A | 5/1993 | Langford |
| 5,245,845 A | 9/1993 | Langford |
| 5,277,868 A | 1/1994 | Langford |
| 5,441,622 A | 8/1995 | Langford |
| 5,443,801 A | 8/1995 | Langford |
| 5,482,684 A | 1/1996 | Martens et al. |
| 5,711,921 A | 1/1998 | Langford |
| 5,753,195 A | 5/1998 | Langford et al. |
| 5,906,802 A | 5/1999 | Langford |
| 6,015,529 A | 1/2000 | Lin et al. |
| 6,066,294 A | 5/2000 | Lin et al. |
| 6,156,267 A | 12/2000 | Pai et al. |
| 6,286,527 B1 | 9/2001 | Stanley |
| 6,534,002 B1 | 3/2003 | Lin et al. |
| 6,656,427 B2 | 12/2003 | Lin et al. |
| 6,702,985 B1 | 3/2004 | Taggart et al. |
| 2003/0190257 A1 | 10/2003 | Halstead et al. |
| 2005/0191208 A1 | 9/2005 | Lin et al. |
| 2005/0260107 A1 | 11/2005 | Jackson et al. |
| 2007/0104610 A1 | 5/2007 | Houston et al. |
| 2007/0207054 A1 | 9/2007 | Langford |

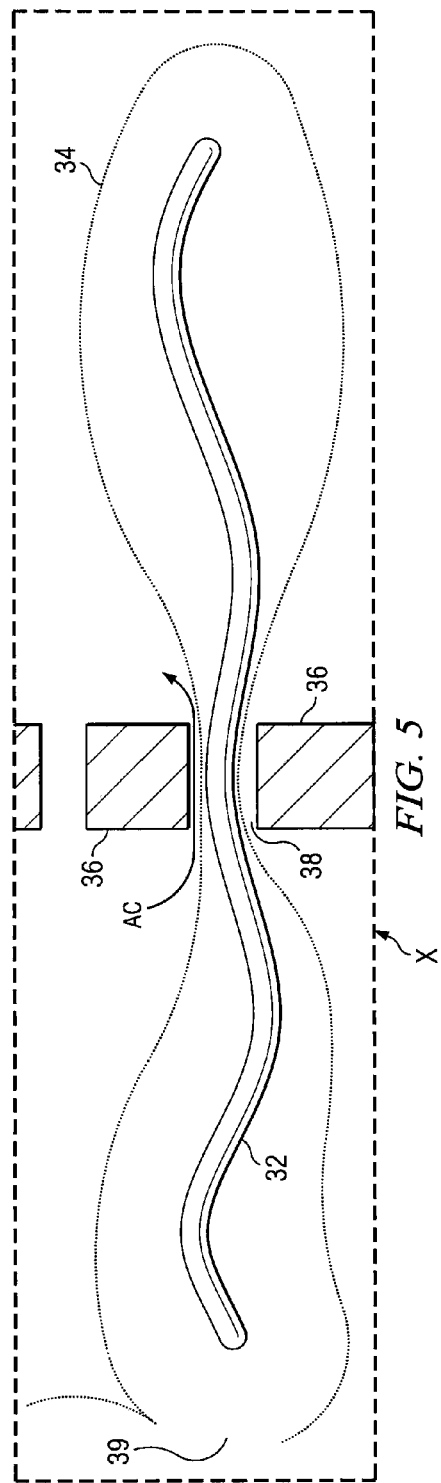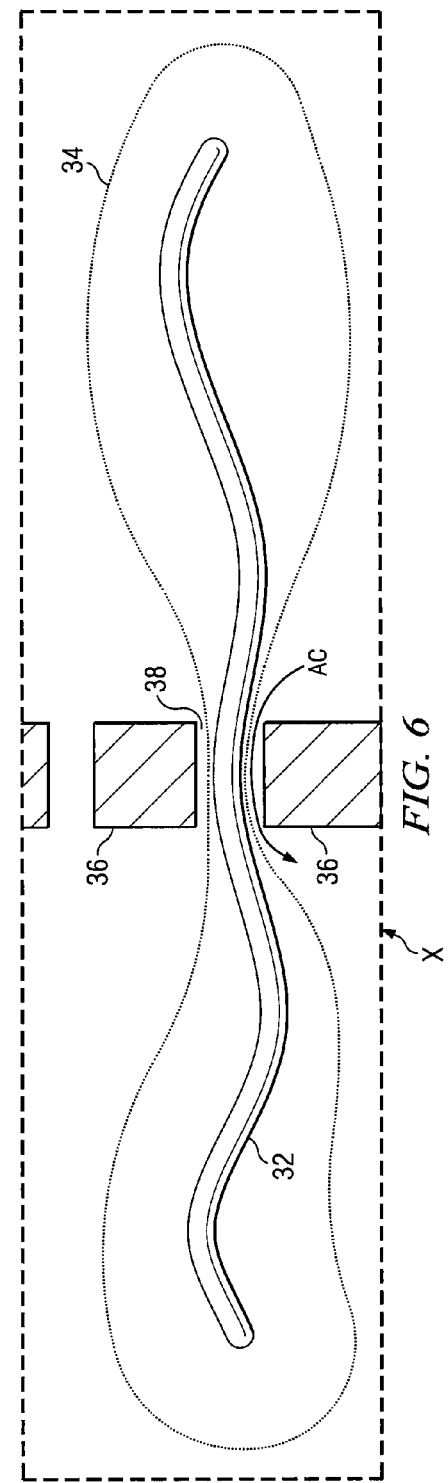

APPARATUS AND METHOD FOR REPROCESSING LUMENED INSTRUMENTS

CROSS-REFERENCE TO RELATED APPLICATION

This application is a continuation-in-part of U.S. patent application Ser. No. 14/152,789, filed on Jan. 10, 2014, which is a continuation of U.S. patent application Ser. No. 12/247,830, filed on Oct. 8, 2008, which is a continuation-in-part of U.S. patent application Ser. No. 11/367,787, filed Mar. 3, 2006, the contents of which are hereby incorporated by reference.

BACKGROUND OF THE INVENTION

1. Field of the Invention

The invention relates generally to improved apparatus and methods for reprocessing items including items with lumens, and, more particularly, to apparatus and methods that involve flowing a liquid between chambers in a divided container containing the item to be processed for cleaning, sterilizing, pre-treating, rinsing or the like.

2. Description of the Related Art

The reprocessing (i.e., cleaning and decontamination) of items that come into contact with the bodily substances of people or animals such that they are substantially "substance free" (of, e.g., viruses, bacteria, detergent, sterilant, lipids, etc.) represent an immense and ongoing challenge. This challenge has been underscored by a recent article entitled "Widely used sterilizer under attack" (published in Jan. 21, 2003 edition of the newspaper *USA Today*). The article describes a fatal outbreak of bacterial infection that was linked to the improper sterilization of hospital bronchoscopes. Despite the hospital's use of one of the most popular sterilizing systems, tests performed by the Centers for Disease Control and Prevention found bacteria on the system's water filters and in its rinse water. This and other infection outbreaks have led to continuing controversy over how best to clean and sterilize used endoscopes. These challenges persist to the present day.

The contaminants typically found on items such as tubular or "lumened" medical items, e.g. endoscopes, are especially difficult to remove. In addition to fecal mater, loose cellular debris, blood and blood products, viruses, and bacteria, an endoscope can be coated with various hydrophobic films, such as "biofilm" material. A biofilm typically comprises cells, both dead and alive, cell debris and extracellular polymer substances. Once biofilm is formed by microorganisms (including bacteria, fungi, and protozoans), these microorganisms can colonize and replicate on the interior surfaces of tubing, forming a protective slime layer known as a "glycocalyx" that is especially difficult to remove.

Merely soaking endoscopes in a sterilant or detergent is unacceptable since numerous pockets exist within the tubing where the sterilant or detergent cannot reach effectively, which leaves areas of contamination within the endoscope. Moreover, with the prevalence of highly contagious diseases such as hepatitis B and C and Acquired Immune Deficiency Syndrome, as well as the pathogens MRSA (Methicillin-resistant Staphylococcus aureus) and Clostridium difficile, reliable sterilization or disposal of all used medical tools seemingly becomes mandatory. Yet, while many medical instruments today are routinely cleaned, disinfected, and reused, experts in the field recently have warned that some of the more difficult to clean and sterilize medical items are putting people at risk. For example, the website "myendosite.com" contains scores of recent references involving infection and endoscopy in the news (see myendosite.com/infection_control_media.htm).

Many attempts to improve sterilization apparatus and methods have been tried over the years. For example, a variety of gas sterilization methods has been investigated in the past. Methods using ethylene oxide and other disinfecting gases are widely used for sterilizing a wide range of items, from contact lenses to surgical instruments.

A sterilizing method must effectively kill all organisms, including spores, without damage to the article or goods being sterilized. Moreover, before sterilization can take place, the instrument must be cleaned to the FDA quantifiable validated standard of clean. Indeed, no reprocessor on the market can perform this other than the unique "push/pull reprocessors" created by the inventor and described below.

So-called "push/pull reprocessing systems" are automatic apparatuses that include a chamber containing a baffle with one or more openings through which water (or another fluid) surges in a synchronous fashion back-and-forth (hence "push/pull") through the opening or openings in the baffle. When soiled items, such as endoscopes and other lumened instruments, are placed within an opening in the baffle, fluid also surges upon and through them. Accordingly, a back-and-forth "scrubbing action" is created by the surging fluid the contacts any accessible surface on an item, including any lumen or lumens.

For example, U.S. Pat. No. 5,711,921 by Langford discloses a medical apparatus cleaning mechanism that includes a container having a first chamber and a second chamber, with the container adapted to accept a medical instrument such that a first portion of the medical instrument lies in the first chamber and a second portion of the medical instrument lies in the second chamber. Pumping means then simultaneously increase fluid pressure within the first chamber of the container while decreasing fluid pressure within the second chamber until the cycle is reversed, i.e., the fluid pressure in the second chamber increases while the fluid pressure in the first chamber synchronously is decreased.

While the Langford apparatus is known to provide superb cleaning and sterilization, the teachings of the Langford patent appear limited to the use of the apparatus with a single-size lumen diameter and do not specify how to evacuate the entire lumen volume per each change in fluid flow direction (i.e., a "stroke").

U.S. Pat. No. 6,534,002 by Lin further notes alleged shortcomings of the teachings in Langford as follows: "One significant problem with this surging mechanism for cleaning endoscopes results from the fact that endoscope channels often have different diameters at their opposite ends. As fluid flows from the larger-caliber end of an endoscope channel to the smaller-caliber end, particulate matter and human tissue, secretions, and excrement can become lodged in the smaller-caliber end and extremely difficult to extract. Another problem with the surging mechanism results from the frequent change in directional flow of fluid through the channels of an endoscope. In cleaning an endoscope, debris must travel a long distance, sometimes more than 150 cm, to traverse the length of the endoscope before the debris can exit the endoscope. In surging methods of cleaning endoscopes, some fluid, debris, and air pockets may move back and forth within the endoscope channel, but never travel far enough to exit the channel before the next directional shift in flow occurs. Thus, some debris and air pockets can remain trapped in the central portion of an endoscope channel with the surging method of cleaning."

The main thrust of how the Lin patent proposes to deal with these shortcomings involves generating a flow of sanitizing solution through a lumened instrument in predominantly one direction, from the smaller-caliber end to the larger-caliber end, to clean or sterilize the inner surface of the device.

However, flowing a fluid in "predominantly one direction" does not necessarily result in better cleaning or sterilizing action; indeed, material may become trapped in complex lumened instruments (such as a restrictor valve in a colonoscope or the spring and guide wire of a biopsy forceps) if a recurring back-and-forth motion is not used to dislodge it.

From the above, it can readily be seen that complex lumened medical devices present unique challenges. Some instruments (e.g., a bronchoscope) have a main lumen of one diameter and another lumen of smaller diameter branching off the main lumen, presenting two resistance ratings inside the same instrument. Furthermore, various lumened instruments have restrictor valves inside the lumen narrowing the fluid path in one direction. This acts as a point of blockage or increased resistance if debris is pushed up against the restrictor. Thus, for those devices that have different size internal lumens in the same instrument, as well as for those that can be 6 feet or longer in length (e.g., a colonoscope), resistance to fluid flow during cleaning and sterilization presents a difficult problem.

Accordingly, it would be desirable to provide an apparatus and methods that carry out effective cleaning and sterilization of even complex lumened instruments quickly and thoroughly, while reducing undesirable effects. In addition, it is desirous that the fluid flow about the exterior of a lumened instrument cause sufficient turbulence to clean the outside of the instrument as well.

SUMMARY OF THE INVENTION

The invention generally involves methods and apparatus for reprocessing items, such as medical or dental items. According to one aspect of the invention, a lumened instrument reprocessing apparatus is provided. The apparatus includes two chambers and a holder to connectorlessly secure a lumened instrument such that a first portion of the lumened instrument lies in the first chamber and a second portion of the instrument lies in the second chamber, a liquid medium contained within the two chambers, and pumping means for simultaneously increasing fluid pressure within the first chamber of the container while decreasing fluid pressure within the second chamber of said container in a reciprocating fashion. The pumping means is designed to displace at a substantially constant pressure at least a total internal volume of the liquid medium through the lumen for a given highest volume of a lumened instrument during each stroke.

In another embodiment, an item is cleaned within a push/pull reprocessing apparatus, contained within sterilizable packaging, and sterilized within the reprocessing apparatus through the introduction of a sterilant, the flow of which includes fresh or new sterilant, such as steam, at one or more times during the sterilizing cycle. Thus, a device can be removed from the apparatus in a sterile package, thereby maintaining post-processing sterility.

In still another embodiment, the invention includes methods of processing an item secured in a connectorless fashion in a push/pull reprocessor, with the push/pull reprocessor including a container having a first chamber and a second chamber and a pressure sensor in each chamber. The methods include the step of generating a flow of a fluid between the first and second chambers and contacting the instrument.

A removable baffle plug of the invention is provided to allow for the placement of different sized items within the baffle, to modulate the pressure between parts of the chamber on either side of the baffle, and to provide information about what is being placed in the chamber through the use of radio frequency identification devices. The plug allows flow between the device being held and the interface, thereby creating a turbulent flow to clean the device exterior in each direction.

In another embodiment, the pressure within both chambers of the push-pull apparatus is kept substantially constant. For example, the pumping means is used to keep the pressure around 12.5 psi in some embodiments of the invention.

In accordance with the above methods, there is provided new and improved apparatus for sterilizing an item.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

BRIEF DESCRIPTION OF THE DRAWINGS

FIG. 5 schematically illustrates an enlarged view of section X taken from FIG. 4.

FIG. 6 schematically illustrates the same enlarged view as FIG. 5 but with the packaging around the item closed.

DETAILED DESCRIPTION OF THE PREFERRED EMBODIMENTS

The terms "push/pull apparatus," "push/pull system," "cleaner/sterilizer," "push/pull reprocessor," "reprocessor," and "reprocessing" as used throughout the specification are meant to be synonymous with the use of a push-pull apparatus (such as the Langford IC Systems, Inc. Manzi Mach 1) that cleans items (e.g., endoscopes, dental appliances, surgical instruments and the like) by surging fluid back-and-forth upon the accessible surfaces of these items.

The term "bi-directional" means flowing in two directions at once within the container of the invention.

As used herein, the term "plasma" is intended to include any portion of the gas or vapors which contains electrons, ions, free radicals, and the like produced as a result of an applied electrical field, including any accompanying radiation that might be produced. While radiation in the radio frequency range is most commonly applied, a broad frequency range may be used.

Figure 1:
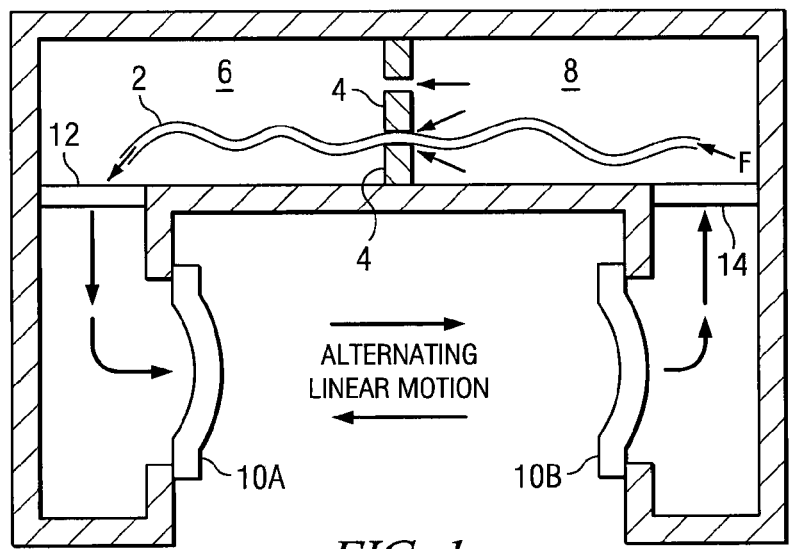
FIG. 1 depicts in a cross-sectional view a "push-pull" reprocessing apparatus of the prior art.

Turning to the figures, wherein like numbers designate like features, FIG. 1 depicts a "push-pull" reprocessor of the prior art. An item with a lumen 2 is secured within an opening of a baffle 4 that divides the reprocessor into a first chamber 6 and a second chamber 8. When valves 12 and 14 are opened and diaphragms 10A and 10B are simultaneously activated in opposite directions as shown, fluid F flow through and around the lumen 2. By reversing the direction of the diaphragms 10A and 10B in unison, a linear or unidirectional flow is created first one way and then the other, resulting in a periodic shear force or "scrubbing action."

Figure 2:
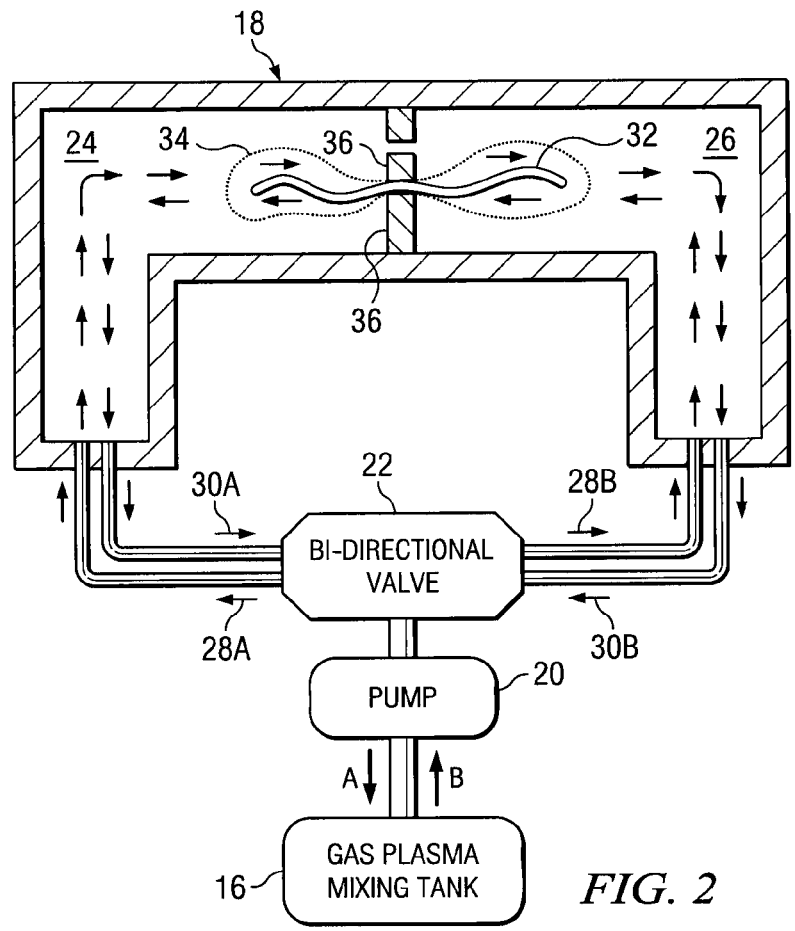
FIG. 2 schematically illustrates a first apparatus and method embodiment of the invention.

FIG. 2 illustrates in simple schematic form a first embodiment of the invention. Unlike the linear flow of an initial quantity of "old" sterilant and "push/pull" action created by the apparatus of FIG. 1, this embodiment of the invention bi-directionally flows fresh sterilant into chamber 18. Thus, for example, mixing tank 16 housing gas plasma is distributed into chamber 18 via a pump 20 and a bi-directional valve 22. The bi-directional valve 22 conveys plasma into first chamber 24 and second chamber 26 at the same time, resulting in a bi-directional flow (indicated by arrows 28A and 28B for inflow and arrows 30A and 30B for outflow when the pump is reversed) over item 32 and gas permeable packaging 34. Reversing the pump at desired intervals (e.g., 2 seconds as shown) allows for at least partial evacuation of "old" sterilant while introducing fresh or "new" sterilant upon the item 32.

While a chamber 18 containing a baffle 36 is shown in this and other embodiments, it should be understood that the invention may include a chamber with no baffle and into which an item is simply placed or secured to a clamp or other structure within the chamber. Moreover, the invention is not limited to gas plasma. Other sterilants may include, for example, ethylene oxide or steam.

In view of the above apparatus and explanation, a method for sterilizing an item encompasses: placing an item 32 within an opening in baffle 36 such that the item 32 extends into the first chamber 24 and second chamber 26, introducing the sterilant into the first and second chambers such that the sterilant is made to flow bi-directionally (28A, 28B, 30A, 30B) in the chambers, and sterilizing the item while introducing fresh sterilant (symbolized by arrows A and B) into the chamber 18 at least once during a sterilizing cycle.

The methods of the invention are especially suitable for sterilization of an item inside a gas-permeable sleeve or packaging 34, because the lack of linear flow or substantial "back and forth" motion reduce the chances that the packaging will be damaged or lost (through, for example, being impaled by the item 32 or by sliding off as a result of being pulled in one direction). In the embodiment shown in FIG. 2, this is accomplished by introducing and evacuating the sterilant on each side of said baffle to provide a continuous bi-directional flow upon item 32.

Figure 3:
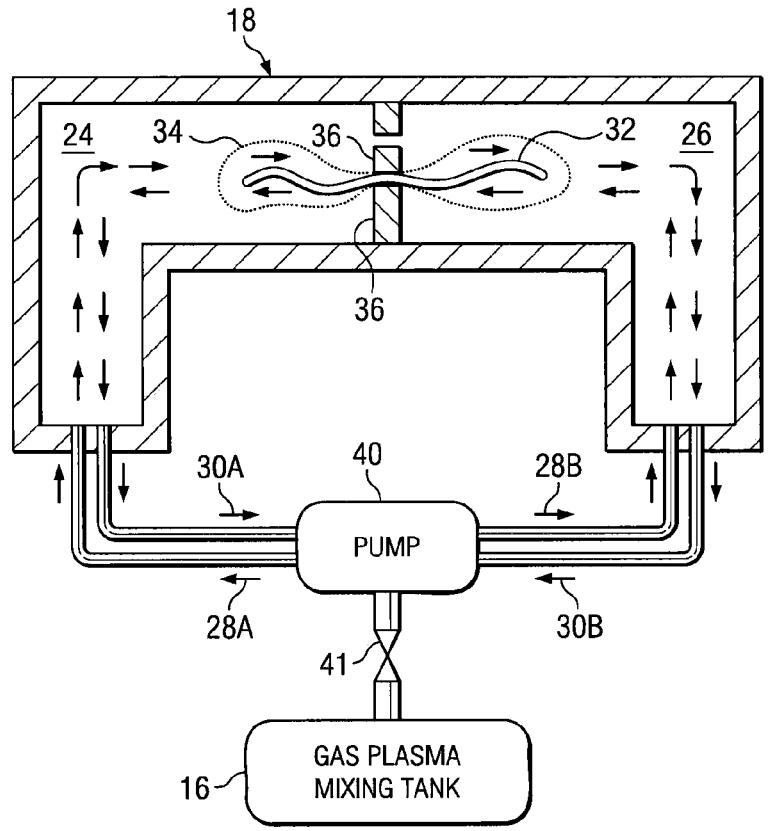
FIG. 3 schematically illustrates a second apparatus and method embodiment of the invention.

In another embodiment of the invention pictured in FIG. 3, gas plasma from tank 16 is alternately introduced on each side of baffle 36 through reversing the one-way pump 40 (during periods in which valve 41 is open). Because sterilant is introduced into only one of chambers 24 or 26 at a time, this embodiment initially appears to provide a "uni-directional" flow of fresh sterilant suitable for sterilizing an item with a lumen. However, as the one-way pump is reversed periodically, the net effect is have gas flowing within the apparatus 18 dynamically to both chambers, with new sterilant being introduced as desired by opening valve 41.

Figure 4:
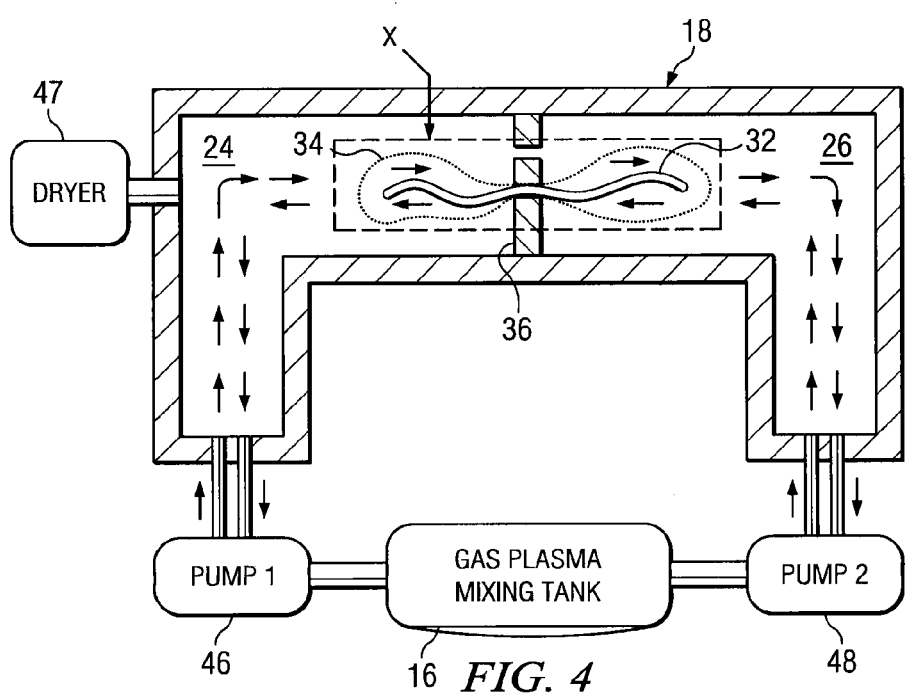
FIG. 4 schematically illustrates a third apparatus and method embodiment of the invention.

FIG. 4 illustrates a third embodiment of the invention. Here, the bi-directional flow of sterilant from mixing tank 16 is created by a plurality of pumps 46 and 48. Similar to the one-way pump show in FIG. 3, a net bi-directional flow effect is created by alternating between pump 46 and 48. Moreover, pumps 46 and 48 can be used at the same time to create a "pulsing" effect, whereby waves of fresh sterilant are introduced into chamber 18. The pumps may provide a continuous flow of fresh sterilant or may pump the existing sterilant (though the use of valves or a bypass (not shown) with the mixing tank 16), with new sterilant being introduced as desired.

In some applications, it may be preferred to dry an item prior to introducing a sterilant. Thus, drying means 47 is connected to chamber 18 to provide heated air. Alternatively, alcohol (e.g., 70% ethanol) or a vacuum can be provided in order to dry item 32.

FIGS. 5 and 6 are greatly enlarged views of section X of FIG. 4. Thus, opening 38 in baffle 36 is more clearly seen. Preferably, the item 32 is contained in a bag 34 having a sealable end 39 (e.g., such as by adhesive) and is placed into opening 38. Also preferably, the item 32 and opening 38 have a "wet fit," meaning that the friction between the opening and the item is such that fluid (including a gas) can flow between different sides of the baffle 36 as shown by arrow AC.

Figure 7:
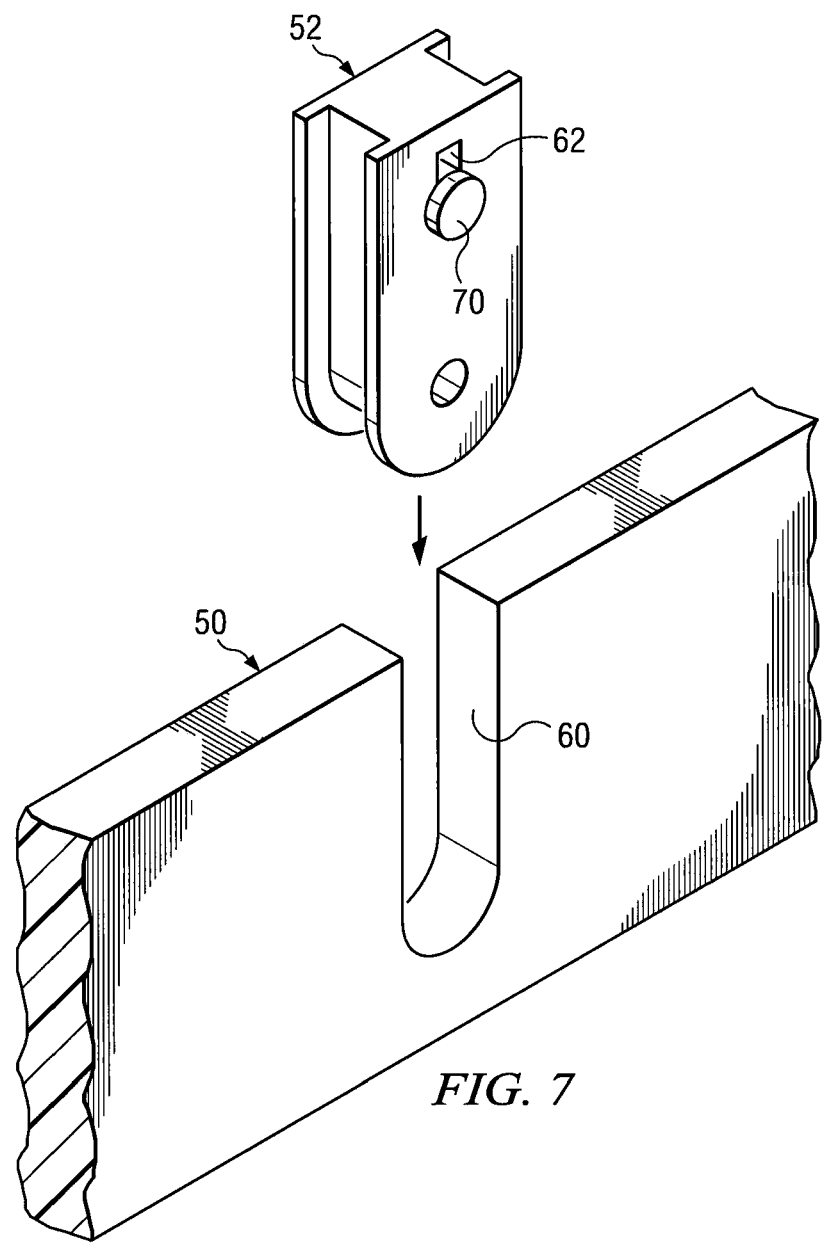
FIG. 7 shows a removable baffle plug of the invention.

To control the flow between different sides of baffle, and to make the baffle adaptable to different sized items, one or more removable plugs may be used with the invention. Turning to FIG. 7, baffle 50 has a removable plug 52 that is disposed within notch 60 and in sealed arrangement therewith. Thus, plugs with different sized openings 62 may be utilized for different sized items. Moreover, one or more plugs 52 may be removed or filled in to change the flow dynamics between chambers on either side of the baffle.

Also, radio frequency (RF) transmitters and receivers can be used in conjunction with the plug of the invention. Thus, RF device 70 disposed upon plug 52 can be used to identify a compatible item also containing a RF device. For example, RF device 70 could identify a bronchoscope placed within the opening 62 of plug 52 and transmit such information to the operator of the sterilizing apparatus so that a particular program or cycle could be employed.

The pressure present within a push-pull apparatus during reprocessing operations should be kept substantially constant to avoid collapsing the lumen passage. Moreover, constant pressure during each stroke best ensures that a given flush volume will travel through each lumened instrument every time (i.e., the lumen flush volumes are maximized and consistent for each stroke). However, in view of the variations and complexity of lumened instruments, it can be problematic to thoroughly clean and sterilize them through evacuation of the lumen in both directions at a consistent pressure.

Previous reprocessor apparatus, such as the FDA cleared Manzi Mach 1 Cleaner Processor System, use a basic control scheme to generate the process pressures that result in fluid flow through instrument lumens. This control scheme employs a reciprocating pump operating at a constant speed. The constant speed control scheme operates the pump at a constant speed independent of the resulting pressure. Thus, the resulting pressure produced is a product of (i) the volume of fluid (ratio of chamber fluid to chamber air) and (ii) the baffle restriction that divides the chamber into two halves. Since the volume of fluid delivered into the chamber can be different from one cycle to the next (this is due, in part, to the available municipal water pressure supplied and the precision of the sensors detecting fluid level), different operating pressures can result.

This range in chamber operating pressures causes the following: Large chamber structure to account for high pressure, reduced fluid flow through instrument lumen at low pressure, increased fluid flow through instrument lumen at high pressure, and reduced margin on instrument pressure rating. This constant speed control scheme also produces large transient pressures and transient pressure drop-outs which occur due to the fluid dynamics. In other words, there is no active control of the operating pressure.

Thus, the invention relates to controlling the pressure and amount of fluid that is moved from one side of a divided chamber to the other such that the fluid is in excess of the total internal volume of the lumened instrument(s) being processed. In other words, at least one entire volume is passed through the lumened instrument(s) being processed for every directional change in fluid flow or "stroke" of a push-pull instrument reprocessor. Moreover, each stroke preferably is performed at a constant pressure. Preferably, the total internal volume of a lumened instrument is exceeded by at least 1% to better ensure that any effects on flow dynamics caused by changes in diameter or the presence of other structures inside the lumen are accounted for.

Thus, the inventor has developed an improvement to the above scheme by actively controlling the operating chamber pressure, thereby producing more consistent flow through instrument lumens and further reducing the possibility of instrument damage. The active pressure control scheme implemented is known as a PID controller (proportional, integral, derivative controller) and can be implemented in hardware or software or a combination. In one embodiment, this improvement is implemented in software.

The PID software design relies upon acquiring (reading) pressure values from two pressure sensors within the reprocessor container and adjusting the pump rate (speed) so as to cause the pressure to remain within a defined range (target range). The PID controller implements the following:

Proportional (error)=present behavior
P=(requested pressure−actual pressure)/Requested pressure
Integral=past behavior
I=(previous I)+P
Derivative=future behavior
D=P−(previous P)
⇒ A scaling value is calculated: S=pScale*P+iScale*I+dScale*D

| Variable | Coefficient |
|---|---|
| Startup Values | |
| pScale | 0.06 |
| iScale | 0.02 |
| dScale | −0.02 |
| Operational Values | |
| pScale | 0.04 |
| iScale | 0.02 |
| dScale | −0.03 |

⇒ The motor speed is adjusted: Target speed=Target speed+S*Target speed

The result of the pressure control algorithm above is that sufficient fluid flow is generated at a controlled (constant or substantially constant) pressure to clean the inside of complex lumened devices of practically any length, even with restrictor valves in place or guide wires and other similar obstacles to normal fluid flow. Also, by completely evacuating the entire lumen(s) volume every stroke, consistent turbulence is created to clean the outside of the instruments and any other non-lumened instruments placed in the same chamber.

Figure 8:
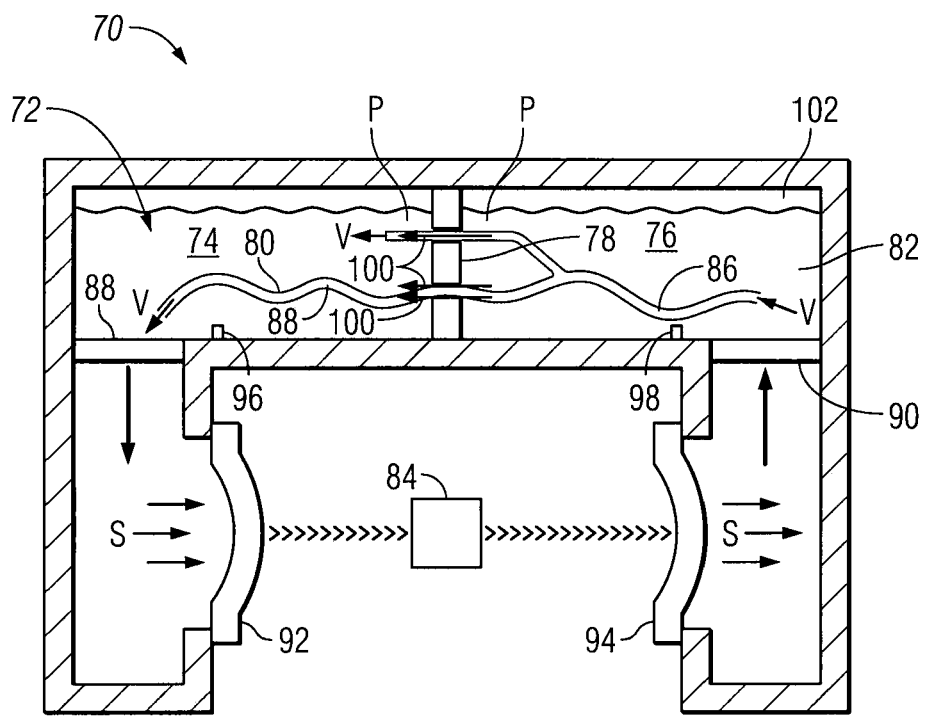
FIG. 8 schematically illustrates another embodiment of the invention.

Turning to the simplified schematic diagram shown in FIG. 8, a reprocessing apparatus 70 is shown that includes a container 72 having a first chamber 74 and a second chamber 76 that are divided from each other by a holder 78 to connectorlessly secure a multi-branched lumened instrument 80. Ideally, a first portion of the lumened instrument 80 lies in the first chamber 74 and a second portion lies in the second chamber 76.

A liquid medium 82 is contained within both chambers of the container and is surged back-and-forth by a pumping means 84 that generate a stroke by simultaneously increasing fluid pressure within the first chamber of while decreasing fluid pressure within the second chamber. The pumping means 84 is controlled to displace at least a total internal volume (V) of the liquid medium 82 through the lumen 86 of instrument 80 during each stroke (even when different diameters are present within the instrument, such as that caused by restrictor valve 88). Thus, for example, a signal is sent to open valves 88 and 90, whereupon pumping means 84 acts upon diaphragms 92 and 94 to generate a stroke (symbolized by arrows S) of fluid flow.

The pumping means 84 is controlled to generate a substantially constant pressure P within both chambers of the container 72. Preferably, constant pressure of between 1-29 psi is achieved. Pressure is maintained according to pressure sensors 96 and 98, which readings from each chamber 74, 76 inform the pumping means to vary its motor speed as needed to ensure that the pressure within each chamber remains substantially constant.

The instrument 80 preferably has a "wet fit" within the holder 78 that allows flow between the device being held and an opening of the holder, thereby creating a turbulent flow 100 to clean the instrument exterior.

The inventor has found that not filling the container 72 to the top with fluid 82 results in better cleaning dynamics, particularly of instrument exteriors. Thus, preferably the container 72 includes a volume of air 102 of between 1-25% at the container top (e.g., 95% fluid, 5% air). The inventor has tried air volumes of up to 25% with good results.

In view of the apparatus shown in FIG. 8, a method for processing (e.g., cleaning and/or sterilizing) an item is provided. In some cases, an item has a lumen. A reprocessor having a back-and-forth motion and including a container having at least one interface that separates the container into two or more chambers or compartments is utilized, with each chamber or compartment having a pressure sensor as disclosed in FIG. 8, for example. An item such as a medical or dental instrument is engaged in a connectorless fashion (i.e., its ends are not coupled with a fitting that shoots fluid upon the instrument and/or within the instrument lumen if one is present) within an opening in the interface. Then, a flow of a fluid from inside the container is generated such that it moves back-and-forth between the two chambers. Preferably, the flow exceeds the total internal volume of a given lumen (if one is present) by at least 1% to ensure full flow-through of even very complex lumened instruments. Also preferably, the back-and-forth flow of fluid occurs at a substantially constant pressure. Ozonated liquid has been found to perform exceptionally well with this method as further described below.

Within the following examples, endoscopes or other medical or dental instruments will be used as an example of an item or instrument to be reprocessed. However, the inventor contemplates use of the invention with any tubular item, as well as a variety of other items such as circuit boards, cosmetic instruments, food preparation instruments, and other items in which reliable cleaning and sterility are desirable or required.

EXAMPLE 1

This example utilizes the apparatus shown in FIG. 8. After securing a lumened instrument with baffle fittings designed for different size lumened instruments with one opening of the lumened instrument in one side of the divided container and the other in the other side of the container. Both chambers of the container are filled to 95% of total container volume with filtered water containing an effective amount of a cleaning agent. The reprocessing apparatus is activated and one side is brought to a positive pressure and the other to a negative pressure and reversed for 10 minutes by the pumping means. During each stroke of the reprocessor, a pressure sensor in each chamber of the divided container monitors the pressure and provides feedback used by a controller to adjust the speed of the pumping means such that a substantially constant pressure is maintained at 12.5 psi.

EXAMPLE 2

The purpose of this test is to document the results of engineering characterization testing performed on a automatic endoscope reprocessor, the Langford I.C. Systems Sterilizer Cleaner (see U.S. Pat. No. 5,906,802 for layout and guidance in the use of this reprocessor). Testing was performed on a Cleaner, Sterilizer Breadboard.

The biopsy lumen of three bronchoscopes were loaded with Birmingham Soil (much more than required by FDA test standards) and inoculated with pathogens from an American Society of Test Methods kit. The scopes were left sitting for a 24 hour time period to permit some drying. Using the same Langford I.C. Systems Sterilizer Cleaner liquid-displacement settings as described, each bronchoscope was subjected to one wash cycle at 10 psi for 5 min with a use concentration of 2.5% of enzymatic cleaner in 10 liters of water. The preferred rate of "liquid displacement" (i.e., the back-and-forth liquid cycling rate in the item-washing chamber of the Sterilizer Cleaner) is 1 gallon per 2 seconds.

Upon completion of the cleaning cycle, and if gas plasma use is desired, the bronchoscope is dried for 5 minutes with heated air and the sterilization cycle could take place by flowing gas plasma for 5-30 minutes upon the bronchoscope. At least once after the beginning of the sterilizing cycle, fresh gas plasma is pulsed into the chamber to better ensure all surfaces are contacted with active sterilant.

EXAMPLE 3

A surgical item is placed in a multi-chamber reprocessor and cleaned as above. The item is then packaged and sealed in a cellulose envelope and transferred to a chamber separate from the cleaning chamber. The separate chamber includes a fluid port to bi-directionally inject gas into the chamber, with a pump alternately applying positive pressure to the chamber and a vacuum to evacuate the chamber. The separate chamber includes radio frequency electrodes to generate the requisite radio frequency signal. The plasma is generated by evacuating the chamber, introducing a gas or vaporized liquid and turning on the power to the electrodes. The plasma is generated in the present process in the same manner as in known prior art plasma sterilization system (e.g., U.S. Pat. No. 4,643,876). The surgical item is exposed from 5-30 minutes to the plasma.

By way of example, hydrogen peroxide is injected in the form of an aqueous solution of hydrogen peroxide containing from about 3% to 20% by weight of hydrogen peroxide. The concentration of hydrogen peroxide vapor in the chamber may range from 0.05 to 10 mg of hydrogen peroxide per liter of chamber volume. A concentration of 0.125 mg per liter is the minimum preferred concentration of hydrogen peroxide. Air or an inert gas such as argon, helium, nitrogen, neon or xenon may be added to the chamber with the hydrogen peroxide to maintain the pressure in the chamber at the desired level. The hydrogen peroxide solution may be injected in one or more separate injections. Since the hydrogen peroxide is decomposed into non-toxic products during the plasma treatment, no additional steps are required to remove residual hydrogen peroxide from the sterilized object or its packaging prior to use of the object.

Alternatively, if sterilization of a lumened instrument (e.g., a bronchoscope) is desired, the above method could be modified for use in a push/pull reprocessor to flow gas plasma upon all accessible surfaces, including the exterior and through the lumen of the scope (before or after any packaging of the item takes place). "Unidirectional" flow (with occasional reversal of direction) would be employed to urge the gas plasma (or other vapor-phase sterilants, such as steam) to effectively permeate through the entire lumen.

EXAMPLE 4

To prove disinfection to the FDA requires the disinfecting medium to kill mycobacterium terrae for high level disinfection and bacillus subtilis to prove sterilization. By soaking in an ordinary aqueous solution of ozonated liquid such as water, the required contact time is approximately 40 minutes to kill bacillus subtilis at a concentration that will cause the least amount of corrosion. For example, a 90% reduction of *B. subtilis* is achieved at 0.10-PPM of ozone for 33 minutes. However, it has been found that if this same concentration of ozone is used in conjunction with the disclosed push/pull device, the contact time is less than 5 minutes because the ozone is delivered to all the surfaces continuously.

This synergistic effect occurs even when the instrument consists of narrow lumens and even more so when the lumens are longer than 24 inches. The ozone is delivered already in solution to the chambers and the surge action delivers the ozone to all surfaces of any instrument both inside and outside to maximize contact time and at lower concentrations than required if the instrument were to be merely soaked in an ozone solution. Moreover, the generating step of the method can be performed at a pressure or speed such that an amount of time required to kill a given pathogen is lessened for a given concentration of ozone in the ozonated liquid.

Preferably, fresh ozone is continuously introduced into the ozonated liquid such that a contaminant in or on an item in the reprocessor is continuously exposed to fresh ozone. The ozone may be supplied from systems know in the art, such as by systems including an oxygen generator, ozone generator and water chiller. The chambers are continuously fed with ozonated water and replenished or boosted with ozone injected directly into the chamber using, for example, either a venturi feed in an aqueous solution or ozone through a diffuser.

A benefit of using a connecter less push/pull system with a controlled pressure differential between the separated chambers is to ensure contact with all surfaces and maximum contact in lumened instruments containing restrictor valves and/or differing diameters and length. The lessening of the contact time in the reprocessor cuts down dramatically on the corrosive effects of ozone on surgical and diagnostic instruments versus the long contact time needed to achieve the same results if the instruments are soaked in an ozone solution. Because ozone has a life span of 33 minutes on average and the soaking time would exceed it in order to kill bacillus subtilis and the only manner in which this could be mitigated is to increase the concentration of ozone thereby damaging or destroying the instrument.

Using ozone in an aqueous solution is synergistic to the push pull system controlled by pressure sensors to maintain a pressure differential, e.g. of 1 psi between the chambers, in that its effectiveness lessens the concentration of ozone and/or contact time required to disinfect the instruments versus soaking them in an aqueous ozone solution thereby mitigating the corrosive properties of ozone at high concentrations over a longer contact time.

By way of further example, a method of preventing or reducing biofilm in an empty push/pull reprocessor having a pressure sensor in each chamber also is contemplated. The reprocessor generates a flow of a sanitizing liquid, such as ozonated liquid, between the first and second chambers. Preferably, ozone is continuously added to the liquid such that the surfaces of the chambers, the baffle, and all other areas in contact with the liquid are exposed to the ozone. Moreover, because of the surging action controlled by the pressure sensors, any existing biofilm is reduced by the "sheering action" of the liquid.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products. All references cited in this application are hereby incorporated by reference herein.

What is claimed is:

1. A method of processing an item secured in a connectorless fashion in a push/pull reprocessor, said push/pull reprocessor including a container having a first chamber and a second chamber and a pressure sensor in each chamber, the method comprising the step of:
   generating a flow of a fluid between said first and second chambers and contacting said item.

2. The method of claim 1, wherein said fluid is an ozonated liquid.

3. The method of claim 2, wherein said generating step is performed at a pressure or speed such that an amount of time required to kill a given pathogen is lessened for a given concentration of ozone in said ozonated liquid.

4. The method of claim 2, wherein fresh ozone is continuously introduced into said ozonated liquid such that a contaminant in or on said item is continuously exposed to said fresh ozone.

5. The method of claim 1, wherein said generating step comprises configuring a pumping means in said push/pull reprocessor to vary its motor speed in response to said pressure sensor in each chamber.

6. The method of claim 1, wherein said generating step is performed at approximately 1-29 psi.

7. The method of claim 1, further including securing said item in a baffle plug that generates a flow between the item being held and an opening of the baffle plug, thereby creating a turbulent flow to clean the item exterior.

8. A method of processing a lumened instrument secured in a connectorless fashion in a push/pull reprocessor, said push/pull reprocessor including a container having a first chamber and a second chamber and a pressure sensor in each chamber, the method comprising the step of:
   generating a flow of a liquid back-and-forth through a lumen of said lumened instrument.

9. The method of claim 8, wherein said liquid is an ozonated liquid.

10. The method of claim 9, wherein said generating step is performed at a pressure or speed such that an amount of time required to kill a given pathogen is lessened for a given concentration of ozone in said ozonated liquid.

11. The method of claim 9, wherein fresh ozone is continuously introduced into said ozonated liquid such that a contaminant in said lumen is continuously exposed to said fresh ozone.

12. The method of claim 8, wherein said generating step comprises configuring a pumping means in said push/pull reprocessor to vary its motor speed in response to said pressure sensor in each chamber.

13. The method of claim 8, wherein said flow exceeds the total internal volume of said lumen by at least 1%.

14. The method of claim 8, wherein said generating step is performed at approximately 1-29 psi.

15. The method of claim 8, further including securing said lumened instrument in a baffle plug that generates a flow between the lumened instrument being held and an opening of the baffle plug, thereby creating a turbulent flow to clean the lumened instrument exterior.

16. A method of preventing or reducing biofilm in an empty push/pull reprocessor, said push/pull reprocessor including a container having a first chamber and a second chamber and a pressure sensor in each chamber, the method comprising the step of:
   generating a flow of a sanitizing liquid between said first and second chambers.

17. The method of claim 16, wherein said sanitizing liquid is an ozonated liquid.

18. The method of claim 17, wherein said generating step is performed at a pressure or speed such that an amount of time required to prevent biofilm formation is lessened for a given concentration of ozone in said ozonated liquid versus soaking.

19. The method of claim 17, wherein fresh ozone is continuously introduced into said ozonated liquid such that said chambers are continuously exposed to said fresh ozone.

20. The method of claim 16, wherein said generating step comprises configuring a pumping means in said push/pull reprocessor to vary its motor speed in response to said pressure sensor in each chamber.

* * * * *